(12) United States Patent
Wilson et al.

(10) Patent No.: US 6,503,489 B1
(45) Date of Patent: Jan. 7, 2003

(54) METHOD OF REDUCING OR PREVENTING MALODOUR

(75) Inventors: Craig S. Wilson, Kent (GB); Tony Minhas, Kent (GB); John M. Behan, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/743,088

(22) PCT Filed: Jul. 6, 1999

(86) PCT No.: PCT/GB99/02166

§ 371 (c)(1),
(2), (4) Date: Jan. 5, 2001

(87) PCT Pub. No.: WO00/01357

PCT Pub. Date: Jan. 13, 2000

(30) Foreign Application Priority Data

Jul. 7, 1998 (GB) .............................................. 9814656

(51) Int. Cl.[7] .................................................. A61K 7/32
(52) U.S. Cl. ......................................... 424/65; 424/401
(58) Field of Search .................................... 424/401, 65

(56) References Cited

U.S. PATENT DOCUMENTS

| 4,278,658 A | * | 7/1981 | Hooper et al. ................. 424/65 |
| 4,292,192 A | * | 9/1981 | Hooper et al. ............... 252/132 |
| 5,554,588 A | * | 9/1996 | Behan et al. .................... 512/1 |

FOREIGN PATENT DOCUMENTS

| DE | 44 27 075 | 2/1996 |
| EP | 750 903 | 1/1997 |
| WO | WO 86/04238 | 7/1986 |
| WO | WO 93/25185 | 12/1993 |
| WO | WO 97/09958 | 3/1997 |
| WO | WO 97/32480 | 9/1997 |

* cited by examiner

Primary Examiner—Jose' G. Dees
Assistant Examiner—Konata M. George
(74) Attorney, Agent, or Firm—Morgan, Lewis & Bockius LLP

(57) ABSTRACT

A method for reducing or preventing body malodour by topically applying to human skin a perfume component capable of selectively increasing the population of naturally occurring deodorising micro-organisms on the surface of the skin. The perfume component is preferably capable of inhibiting lysozyme.

13 Claims, No Drawings

METHOD OF REDUCING OR PREVENTING MALODOUR

This invention relates to perfume components, mixtures thereof and perfume compositions, to personal products and detergent products containing such perfumes, and to the use of such perfumes and products to deliver a deodorant effect.

In particular, it relates to perfume components, mixtures thereof, and perfume compositions for inhibiting the production of odorous metabolites by topically applying to human skin perfume components capable of inhibiting the production of body malodour, by selectively increasing the population of naturally occurring deodorising micro-organisms on the surface of the skin.

Typically, a deodorising composition will attempt to significantly reduce or prevent body odour by reducing either perspiration or the number of micro-organisms on the surface of the skin. The former is usually referred to as an antiperspirant composition and the latter a deodorant.

Compositions reducing perspiration often comprise a metal salt, such as an aluminium or zirconium salt which blocks the sweat pores.

Deodorants, on the other hand, reduce the number of micro-organisms on the surface of the skin. It is well known that sweat is odourless until it has been degraded by the skin microflora. Typical deodorants include ethanol and Triclosan (2', 4,4'-trichloro,2-hydroxy diphenyl ether) which are well known antimicrobial agents. However, the deodorising effect obtained with such deodorants wears off rather rapidly as the remaining microflora multiply and recover their numbers.

A criticism of many deodorant actives is that they indiscriminately affect all populations of micro-organism resident on the surface of the skin. This mechanism of controlling body odour may be effective, for a limited period of time, but is thought to be medically undesirable as the skin's natural microflora are often considered the first barrier against disease.

WO 87/106827 (Robertet SA) describes inhibitors of esterase-producing micro-organisms. It is suggested that deodorant compositions may comprise such inhibitors as deodorising actives.

EP-A-0 750 903 (Cooperatie Cosun UA) describes compositions comprising sugar-fatty acid esters which are said to be specific against lipophilic diphtheroids. This reference discloses that this group of micro-organisms is responsible for body malodour.

It is well known that volatile fatty acids (VFAs) play a major role in malodour perception. GB 1 517 042 (Personal Products Company) describes deodorant compositions comprising particular actives for reducing malodour by sub-lethally inhibiting fatty acid formation in Corynebacterium species.

Whereas these prior proposals are mainly concerned with inhibiting the growth of malodour producing micro-organisms, the present invention is concerned with increasing the growth of malodour-reducing micro-organisms.

Accordingly, the invention provides a cosmetic method for reducing or preventing body malodour by topically applying to human skin a composition comprising an active agent capable of reducing malodour, wherein the agent is a perfume component which is capable of selectively increasing the population of naturally occurring deodorising micro-organisms on the surface of the skin.

The invention also provides the use of a perfume component to inhibit lysozyme.

The invention further provides the use of a perfume composition, comprising at least 30% by weight of one or more perfume components capable of selectively increasing the population of naturally occurring deodorising micro-organisms on the surface of the skin, to reduce body malodour.

The invention further provides the use of a deodorant product, comprising a perfume component, to reduce body malodour by selectively increasing the population of naturally occurring deodorising micro-organisms on the surface of the skin.

The invention further provides a perfume composition comprising at least 30% by weight of one or more of the following perfume components; Acetyl tri butyl Citrate (tributyl 2-(acetyloxy)-1,2,3-propanetricarboxylate), Aidehyde C10, Amber AB 358, Amyl Salicylate, Anisyl acetate (4-methoxybenzyl acetate), Cis-3-hexenyl salicylate, Dihydro Eugenol (2-(methyloxy)-4-propyl-1-benzenol), Dupical (4-tricyclo(5.2.1.0 2,6)dec-8-ylidenbutanal), Geraniol pure, Methyi eugenol, Para cresyl methyl ether, Styrallyl acetate, and a deodorant product comprising such a perfume composition.

The invention still further provides a method of producing a perfume composition which comprises (i) evaluating perfume components on the ability to selectively increase the population of naturally occurring deodorising micro-organisms on the surface of the skin, (ii) selecting perfume components on the ability to selectively increase the population of naturally occurring deodorising micro-organisms on the surface of the skin, and (iii) mixing together two or more of said selected perfume components, optionally with other perfume components.

The term "perfume component" is used herein to represent a material which is added to a perfume to contribute to the olfactive properties of the perfume. A perfume component can be acceptably employed to provide odour contributions to the overall hedonic performance of products. Typically, a perfume component will be generally recognised as possessing odours in its own right, will be relatively volatile and often has a molecular weight within the range 100 to 300. Typical materials which are perfume components are described in "Perfume and Flavour Chemicals", Volumes I and II (Steffan Arctander, 1969). A perfume composition will contain a number of individual perfume components, and optionally a suitable diluent. The concentration of perfume components referred to herein is relative to the total concentration of perfume components present in the composition, ie excludes any diluent.

Naturally occurring deodorising micro-organisms are members of the cutaneous microflora which are capable of degrading odoriferous moiecules. By degrading is meant that the odoriferous molecules are transformed, by the deodorising micro-organisms, to molecules which have either no odour, a reduced malodour or a preferred odour. In particular, naturally occurring deodorising micro-organisms include members of the Micrococcus and Brevibacterium genera.

By selectively increasing is meant that the perfume component is capable of increasing the population of deodorising micro-organisms, preferably relative to non-deodorising micro-organisms, and more preferably by inhibiting the action of the anti-bacterial enzyme lysozyme.

Lysozyme is a glycosidase enzyme which degrades certain bacterial cell walls and is found on the surface of the skin. Surprisingly, the population of naturally occurring deodorising micro-organisms on the surface of the skin may be increased by inactivating or reducing lysozyme activity. This may be done by contacting lysozyme with perfume components that block the action of this enzyme.

Deodorant products include but are not limited to body deodorants and antiperspirants including roll ons, gel products, stick deodorants, antiperspirants, shampoos, soaps, shower gels, talcum powder, hand creams, skin conditioners, sunscreens, sun tan lotions, skin and hair conditioners.

It will be recognised that the perfume components, mixtures thereof and perfume compositions may also be usefully employed for deodorant properties in other product areas, notably in laundry and household products such as rinse conditioners, household cleaners and detergent cleaners. These perfume components can be incorporated into textiles themselves during their production using techniques known in the art, to provide deodorant protection The active perfume components may be mixed with an antiperspirant active or an additional alternative functioning deodorising active, examples of which are common in the art. The active components may also be mixed with other perfume components, which are not active against lysozyme, in order to provide perfume compositions that deliver the desired deodorant effect and/or hedonistic properties.

The active perfume components listed below may be used to increase the deodorant effect of consumer products. In a preferred methos according to the invention, an Odour Reduction Value, measured as described in Example 2, of at least 10%, more preferably at least 30%, and particularly at least 50% is obtained. To deliver high deodorant effects these active components suitably comprise at least 10%, preferably at least 30%, more preferably at least 50%, and particularly at least 60% by weight of the total perfume formulation. A deodorant product preferably comprises at least 0.05% to 4%, more preferably 0.1% to 2% by weight of the active perfume components. Preferred actives include the following perfume components.

Acetyl tri butyl Citrate (tributyl 2-(acetyloxy)-1,2,3-propanetricarboxylate)

Aldehyde C10

Amber AB 358

Amyl Salicylate

Anisyl acetate (4-methoxybenzyl acetate)

Cis-3-hexenyl salicylate

Dihydro Eugenol (2-(methyloxy)-4-propyl-1-benzenol)

Dupical (4-tricyclo(5.2.1.0 2,6)dec-8-ylidenbutanal)

Geraniol pure

Methyl eugenol

Para cresyl methyl ether

Styrallyl acetate

A perfume composition for use in the present invention preferably comprises at least 4, more preferably at least 7, and particularly at least 10 of the above perfume components.

The invention is illustrated by the following examples.

EXAMPLE 1

Test of Lysozyme Inhibition

An overnight culture of Microccocus deposited as NCIMB 13594 (deposited under the Budapest Treaty with National Collections of Industrial and Marine Bacteria Ltd, 23 St Machar Drive, Aberdeen Scotland, UK on Jul. 5, 1999) was centrifuged at 3000 g for 10 minutes to pellet the cells in the bottom of the container. The supernatant was then removed and the pellet was resuspended in 10 ml of Pk buffer. The cells were then washed twice and finally resuspened in fresh buffer. The optical density of the suspension was adjusted using Pk buffer to give a reading of 1.6 OD units at 540 nm.

Stock lysozyme solutions were prepared by adding 2.5 mg of hen egg white lysozyme enzyme to 10 ml of sterile Pk buffer. This was then filter sterilised and stored in a sterile aliquot at 4° C. until needed.

To each well of a 96 well microtitre plate was added 80 $\mu$l of Pk buffer. No ingredients were added to column 1 which acted as the negative control. To the wells A2 and E2 25 ml of the perfume component under investigation was added. After thorough mixing with a pipette 25 $\mu$l of medium was removed from well A2 to well B2. This process was then repeated until well D2 was reached, from this well 25 $\mu$l of medium was removed and discarded. The process was repeated in wells E2 to H2. Individual aliquots (100 $\mu$l) of the previously prepared suspension of the Micrccoccus were then added to wells A2 to H2. The optical density of each well was then measured using a micro-titre plate reader fitted with a wavelength filter set at 540 nm. After this was completed 20 $\mu$l of lysozyme was added to the wells in rows A to D, column numbers 2 to 12. Pk buffer (20 $\mu$l) was added to the wells in rows E to H in columns 2 to 12. The wells in rows A to D acted as the experimental. The wells in rows E to H acted as the component controls to test if the component was responsible for the drop in cell density.

The plate was then incubated at 37° C. for 24 hours before the optical density was again read at 540 nm. If the component was capable of inhibiting the action of lysozyme then a small or no decrease in optical density occurred in the experimental wells.

Pk buffer contained 3.482 g $K_2HPO_1$ and 2.642 g $KH_2PO_4$ in one litre of distilled water Growth of the organism was carried out in a 30 ml sterile universal bottle containing 10 ml of tryptone soya broth (TSB). After inoculation of the broth with a single colony of the Micrococcus, the bottle was incubated for 24 hours at 35° C. in a orbital shaker at 200 rpm. Table 1 lists the perfume components that were shown to inhibit the action of lysozyme at a concentration of 0.2% (or 0.4% where indicated) resulting in an increase in the organism population compared to the blank (no perfume component), and a relative increase in the organism population compared to the control (repeat of lysozyme test with a non-deodorising organism).

TABLE 1

| Inhibition of the action of lysozyme | No inhibition observed |
| --- | --- |
| Acetyl tributyl citrate | Bergamot oil ABX 5638 |
| Aldehyde C10 | Carvone laevo |
| Amber AB 358 | Jasmin (AB 0284A) |
| Amyl salicylate | Lavindin bulked |
| Anisyl acetate (0.4%) | Thymol |
| cis-3-Hexenyl salicylate | Tri-ethyl citrate (0.4%) |
| Dihydro eugenol | Alcohol C 6 |
| Dupical | Allyl amyl glycolate |
| Geraniol pure | Citronellyl nitrile |
| Methyl eugenol | Ethyl salicylate |
| Para cresyl methyl ether | Tonalid |
| Styrallyl acetate | Galaxolide |
|  | Iso-E Super |

Amber AB 358 is supplied by Quest International
Bergamot ABX 5638 is supplied by Quest International
Jasmin AB 0284A is supplied by Quest International
Tonalid - 1-(3,5,5,6,8,8-hexamethyl-5,6,7,8-tetrahydro-2-naphthalenyl)-1-ethanone
Galaxolide - 4,6,6,7,8,8-hexamethyl-1,3,4,6,7,8-hexahydrocyclopentl[γ]isochromene
Iso-E Super is supplied by International Fragrances and Flavours.

EXAMPLE 2

The following are typical formulations of deodorant products which comprise a perfume or perfume component capable of inhibiting the production of body malodour by micro-roransms comprising Corynebacteria. These formulations are made by methods common in the art.

| Ingredient | Content (% by weight) | |
| --- | --- | --- |
| Deodorant Sticks | Sample 1A | Sample 1B |
| Ethanol |  | 7.8 |
| Sodium stearate | 7.0 | 6.0 |
| Propylene glycol | 70.0 | 12.0 |
| Perfume | 1.5 | 2.0 |
| PPG-3 Myristyl ether |  | 28.0 |
| PPG-10 Cetyl ether |  | 10.0 |
| Cyctomethicone |  | 34.0 |
| Inhibitor | 0.2 | 0.2 |
| Water | 21.3 |  |
| Aerosols | Sample 2A | Sample 2B |
| Ethanol B | up to 100 |  |
| Propylene glycol | as required |  |
| Perfume | 2.5 | 1.5 |
| Chlorhydrol microdry |  | 31.8 |
| Silicone fluid DC344 |  | up to 100 |
| Bentone gel IPP |  | 13.65 |
| Irgasan DP300 (optional) | 0.03 |  |
| Dimethyl ether | 20.0 |  |
| Inhibitor | 0.3 | 0.3 |
| Concentrate |  | 22.0 |
| Water | 23.0 |  |
| Roll ons | Sample 3A | Sample 3B |
| Ethanol | up to 100 | 60.0 |
| Klucel MF |  | 0.65 |
| Cremphor RM410 |  | 0.50 |
| Perfume | 0.50 | 1.0 |
| AZTC* | 20.0 |  |
| Cyclomethicone | 68.0 |  |
| Dimethicone | 5.0 |  |
| Silica | 2.5 |  |
| Inhibitor | 0.10 | 0.10 |
| Water |  | 37.75 |

*Aluminum zirconium tetrachlorohydro glycinate

A perfume composition embodying this invention was made and tested for deodorant action in an underarm product, using an Odour Reduction Value test generally as described in U.S. Pat. No. 4,278,658, but with the substitution of the perfumed soap by perfumed roll-on product, using the formulation described in Formulation 3B. The perfume composition and the method for an Odour Reduction Value test are set out below.

| Composition % by weight | |
| --- | --- |
| 0.8 | ALDEHYDE C10 (DECANAL) 50% DEP AA 0213 |
| 15 | ACETYL TRI BUTYL CITRATE |
| 0.2 | ADOXAL |
| 6 | BENZYL ACETATE EXTRA |
| 4 | CIS 3 HEXENYL SALICYLATE |
| 7 | AMYL SALICYLATE |
| 0.5 | CASSIS BASE 345 AB 2967 |
| 1.5 | DIHYDRO EUGENOL |
| 15 | GERANIOL PURE |
| 1.5 | CYCLAMEN ALDEHYDE |
| 0.3 | DUPICAL |
| 4 | HABANOLIDE |
| 5 | MEFROSOL |
| 37 | METHYL IONONE ALPHA ISO |
| 10 | METHYL DIHYDRO JASMONATE |
| 0.5 | PARA CRESYL METHYL ETHER |
| 5 | MUGUET NATURE AB 1951 |
| 2 | ORTHOLATE |
| 8 | PHENYL ETHYL ALCOHOL |
| 2 | STYRALLYL ACETATE |
| 2 | ROSACETONE |
| 6 | TETRAHYDRO LINALOL |

The Odour Reduction Value test was carried out using a panel of 40 Caucasian male subjects. A standard quantity (approximately 0.4 g) of a roll-on product containing one of the perfume compositions or an unperfumed control was applied to the axillae of the panel member in accordance with a statistical design.

After a period of five hours the axillary odour was judged by three trained female assessors who scored the odour intensity on the 0 to 5 scale, as shown below.

| Score | Odour level | Conc. of aqueous isovaleric acid (ml/l) |
| --- | --- | --- |
| 0 | No odour | 0 |
| 1 | Slight | 0.013 |
| 2 | Definite | 0.053 |
| 3 | Moderate | 0.22 |
| 4 | Strong | 0.87 |
| 5 | Very Strong | 3.57 |

Average scores for each test product and the control product were then determined and the score for each test product was subtracted from the score for the control product to give the Odour Reduction Value.

The perfume composition described above contained 45.3% of active perfume components and was particularly effective in the odour reduction value test.

What is claimed is:

1. A perfume composition comprising at least 30% by weight of one or more of the following perfume components:
   Aldehyde C10, Amber AB 358, Anisyl acetate (4-methoxybenzyl acetate), Dihydro Eugenol (2-(methyloxy)-4-propyl-1-benzenol), Dupicl (4-tricyclo (5.2.1.0 2,6)dec-8-ylidenbutanal), Geraniol pure, Methyl eugenol, Para cresyl methyl ether, Styrallyl acetate.

2. A perfume composition comprising at least 30% by weight of at least 4 of the following perfume components:
   Acetyl tri butyl Citrate (tributyl 2-(acetyloxy)-1,2,3-propanetricarboxylate), Aldehyde C10, Amber AB 358, Anisyl acetate (4-methoxybenzyl acetate), Dihydro Eugenol (2-(methyloxy)-4-propyl-1-benzenol), Dupical (4-tricyclo(5.2.1.0 2,6)dec-8-ylidenbutanal), Geraniol pure, Methyl eugenol, Para cresyl methyl ether, Styrallyl acetate.

3. A cosmetic method for reducing or preventing body malodour by topically applying to human skin a perfume composition comprising at least 30% by weight of at least four perfume components capable of selectively increasing the population of naturally occurring deodorising microorganisms on the surface of the skin, wherein said at least four perfume components are selected from the group consisting of Acetyl tri butyl citrate (tributyl 2-(acetyloxy)-1,2, 3-propanetricarboxylate), Aldehyde C10, Amber AB 358, Anisyl acetate (4-methoxybenzyl acetate), Dihydro eugenol (2-(methyloxy)-4-propyl-1-benzenol), Dupical (4-tricyclo (5.2.1.02,6)dec-8-ylidenbutanal), Geraniol pure, Methyl eugenol, Para cresyl methyl ether, and Styrallyl acetate.

4. A method according to claim 3 wherein an Odour Reduction value of at least 10% is obtained.

5. A method according to claim 3 wherein the naturally occurring deodorising micro-organisms are members of the Micrococcus genus or the Brevibacterium genus.

6. A method of inhibiting lysozyme which comprises administering to a host in need of such inhibition, an effective amount of at least four perfume components selected from the group consisting of Acetyl tri butyl citrate (tributyl 2-(acetyloxy)-1,2,3-propanetricarboxylate), Aldehyde C10, Amber AB 358, Anisyl acetate (4-methoxybenzyl acetate), Dihydro eugenol (2-(methyloxy)-4-propyl-1-benzenol), Dupical (4-tricyclo(5.2.1.02,6)dec-8-ylidenbutanal), Geraniol pure, Methyl eugenol, Para cresyl methyl ether, and Styrallyl acetate.

7. A method of reducing body malodour which comprises administering to a host in need of such treatment, an effective amount of a perfume composition comprising at least 30% by weight of at least four perfume components capable of selectively increasing the population of naturally occurring deodorizing micro-organisms on the surface of the skin, said at least four perfume components being selected from the group consisting of Acetyl tri butyl citrate (tributyl 2-(acetyloxy)- 1,2,3-propanetricarboxylate), Aldehyde C10, Amber AB 358, Anisyl acetate (4-methoxybenzyl acetate), Dihydro eugenol (2-(methyloxy)-4-propyl-1-benzenol), Dupical (4-tricyclo(5.2.1.02,6)dec-8-ylidenbutanal), Geraniol pure, Methyl eugenol, Para cresyl methyl ether, and Styrallyl acetate.

8. A method of reducing body malodour which comprises administering to a host in need of such treatment, a deodorant product comprising at least four perfume components in an amount to selectively increase the population of naturally occurring deodorizing micro-organisms on the surface of the skin, said perfume component being selected from the group consisting of Acetyl tri butyl citrate (tributyl 2-(acetyloxy)-1,2,3-propanetricarboxylate), Aldehyde C10, Amber AB 358, Anisyl acetate (4-methoxybenzyl acetate), Dihydro eugenol (2-(methyloxy)-4-propyl-1-benzenol), Dupical (4-tricyclo(5.2.1.02,6)dec-8-ylidenbutanal), Geraniol pure, Methyl eugenol, Para cresyl methyl ether, and Styrallyl acetate.

9. A cosmetic method for reducing or preventing body malodour by topically applying to human skin a perfume composition comprising at least four perfume components capable of selectively increasing the population of naturally occurring deodorising micro-organisms on the surface of the skin, wherein the perfume components are selected from the group consisting of: Acetyl tri butyl citrate (tributyl 2-(acetyloxy)-1,2,3-propanetricarboxylate), Aldehyde C10, Amber AB 358, Anisyl acetate (4-methoxybenzyl acetate), Dihydro eugenol (2-(methyloxy)-4-propyl-1-benzenol), Dupical (4-trcyclo(5.2.1.0 2,6)dec-8-ylidenbutanal), Geraniol pure, Methyl eugenol, Para cresyl methyl ether, and Styrallyl acetate."

10. A method of producing a perfume composition which comprises (i) evaluating perfume components on the ability to selectively increase the population of naturally occurring deodorising micro-organisms on the surface of the skin, (ii) selecting perfume components on the ability to selectively increase the population of naturally occurring deodorising micro-organisms on the surface of the skin, and (iii) mixing together two or more of said selected perfume components, optionally with other perfume components.

11. A method according to claim 10 wherein the selected perfume components are selected from the group consisting of Acetyl tri butyl citrate (tributyl 2-(acetyloxy)-1,2,3-propanetricarboxylate), Aldehyde C10, Amber AB 358, Anisyl acetate (4-methoxybenzyl acetate), Dihydro eugenol (2-(methyloxy)-4-propyl-1-benzenol), Dupical (4-tricyclo (5.2.1.0 2,6)dec-8-ylidenbutanal), Geraniol pure, Methyl eugenol, Para cresyl methyl ether, Styrallyl acetate.

12. A method according to claim 10 wherein the selected perfume components inhibit lysozyme.

13. A deodorant product comprising a perfume composition defined in claim 12.

* * * * *